(12) United States Patent
Ooms et al.

(10) Patent No.: US 6,639,093 B2
(45) Date of Patent: Oct. 28, 2003

(54) PROCESS FOR THE PREPARATION OF HYDROXYBENZOIC BENZYL ESTERS

(75) Inventors: Pieter Ooms, Krefeld (DE); Bernd-Ulrich Schenke, Bottrop (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/117,771

(22) Filed: Apr. 5, 2002

(65) Prior Publication Data

US 2003/0053964 A1 Mar. 20, 2003

(30) Foreign Application Priority Data

Apr. 12, 2001 (DE) .......................................... 101 18 308

(51) Int. Cl.[7] ..................... C07C 255/51; C07C 205/06; C07C 69/773; C07C 69/88

(52) U.S. Cl. .......................... 558/416; 558/415; 560/22; 560/23; 560/53; 560/65; 560/71; 560/72

(58) Field of Search ............................. 560/53, 71, 72, 560/22, 23, 65; 558/416, 415

(56) References Cited

U.S. PATENT DOCUMENTS

| | | | |
|---|---|---|---|
| 4,973,737 A | 11/1990 | Ueno et al. | 560/67 |
| 5,777,151 A | 7/1998 | Crochemore | 560/61 |

FOREIGN PATENT DOCUMENTS

| | | |
|---|---|---|
| JP | 63-218652 | 9/1988 |

Primary Examiner—Joseph K. McKane
Assistant Examiner—Ebenezer Sackey
(74) Attorney, Agent, or Firm—Godfried R. Akorli; Diderico vanEyl

(57) ABSTRACT

The invention relates to the preparation of hydroxybenzoic benzyl esters by reacting benzyl chloride with hydroxybenzoic acids in the presence of one or more amides.

12 Claims, No Drawings

PROCESS FOR THE PREPARATION OF HYDROXYBENZOIC BENZYL ESTERS

BACKGROUND OF THE INVENTION

The present invention relates to a process for the preparation of hydroxybenzoic benzyl esters by reacting benzyl chloride with hydroxy-benzoic acid.

Benzyl salicylate is used as stabilizer in fragrance compositions and sunscreens. Benzyl salicylate and processes for its preparation are already known.

Thus, EP-A 117,502, for example, describes the preparation of benzyl salicylate by esterifying salicylic acid or transesterifying salicyclic esters with benzyl alcohol.

Benzyl salicylate can also be prepared by reacting alkali metal salicylates with benzyl chloride, optionally in the presence of phase transfer reagents (JP-A 63/218652, EP-A 534,817). A disadvantage is the formation of salts that must be disposed of and thus reduce the economic feasibility of these processes.

It was therefore the object to develop, starting from benzyl chloride, a process for the preparation of hydroxybenzoic benzyl esters that can be carried out under mild reaction conditions and leads to good yields in a cost-effective manner.

SUMMARY OF THE INVENTION

The present invention relates to a process for the preparation of hydroxybenzoic benzyl esters of the formula

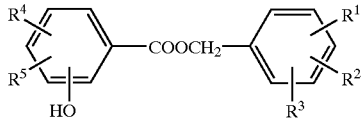

in which $R^1$ to $R^5$ are identical or different and are hydrogen, $C_1$–$C_6$-alkyl, $C_1$–$C_6$-alkoxy, $C_1$–$C_6$-halogenoalkyl, $C_1$–$C_6$-halogenoalkoxy, CN, CO($C_1$–$C_6$-alkyl), $NO_2$, or halogen,
comprising reacting benzyl chlorides of the formula

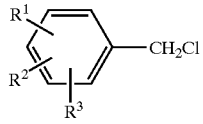

in which $R^1$, $R^2$, and $R^3$ have the meanings given above for the hydroxybenzoic benzyl ester,
or mixtures of such benzyl chlorides and benzyl alcohols of the formula

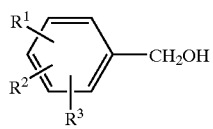

in which $R^1$, $R^2$, and $R^3$ have the meanings given above for the hydroxybenzoic benzyl ester, with hydroxybenzoic acids of the formula

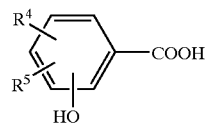

in which $R^4$ and $R^5$ have the meanings given above, in the presence of one or more amides of the formula
$R^6$CON $R^7R^8$
in which
$R^6$ is hydrogen, $C_1$–$C_6$-alkyl, $C_1$–$C_6$-alkoxy, amino, $C_1$–$C_6$-alkyl-amino, $C_1$–$C_6$-cycloalkylamino, or $C_1$–$C_6$-dialkylamino, and
$R^7$ and $R^8$ are identical or different and are hydrogen, $C_1$–$C_6$-alkyl, $C_1$–$C_6$-cycloalkyl, $C_1$–$C_6$-alkoxy, $C_1$–$C_{10}$-aralkyl, or $C_1$–$C_{12}$-aryl,
or $R^6$ and $R^7$ together form a group $(CH_2)_n$ or $NR^9(CH_2)_n$,
in which
$R^9$ is hydrogen, $C_1$–$C_6$-alkyl, $C_1$–$C_6$-cycloalkyl, $C_1$–$C_{10}$-aralkyl, or $C_1$–$C_{12}$-aryl, and
n is 2 to 6.

DETAILED DESCRIPTION OF THE INVENTION

The process according to the invention can be carried out cost-effectively and under mild reaction conditions.

The radicals $R^1$ to $R^5$ generally have the following meanings:

Alkyl is generally a straight-chain or branched hydrocarbon radical having 1 to 6 (preferably 1 to 4, particularly preferably 1 or 2) carbon atoms. Examples which may be mentioned are methyl, ethyl, propyl, iso-propyl, butyl, iso-butyl, pentyl, iso-pentyl, hexyl, and iso-hexyl. Preference is given to methyl, ethyl, propyl, iso-propyl, butyl, pentyl, and hexyl, and particular preference is given to methyl and ethyl.

Alkoxy generally means a straight-chain or branched alkoxy radical having 1 to 6 (preferably 1 to 4, particularly preferably 1 or 2) carbon atoms. Examples which may be mentioned are methoxy, ethoxy, propoxy, iso-propoxy, butoxy, iso-butoxy, pentoxy, iso-pentoxy, hexoxy, and iso-hexoxy. Preference is given to methoxy, ethoxy, propoxy, iso-propoxy, butoxy, iso-butoxy, pentoxy, and hexoxy, and particular preference is given to methoxy and ethoxy.

Halogenoalkyl generally means a straight-chain or branched hydrocarbon radical having 1 to 6 (preferably 1 to 4, particularly preferably 1 or 2) carbon atoms having 1 to 10 (preferably 1 to 8, particularly preferably having 1 to 5) halogen atoms. Examples that may be mentioned are chloromethyl, fluoromethyl, difluoromethyl, trifluoromethyl, fluoroethyl, fluoropropyl, and hexafluorobutyl. Preference is given to fluoromethyl, difluoromethyl, trifluoromethyl, fluoroethyl, fluoropropyl, and hexafluorobutyl, and particular preference is given to fluoromethyl and trifluoromethyl.

Halogenoalkoxy generally means a straight-chain or branched alkoxy radical having 1 to 6 (preferably 1 to 4, particularly preferably 1 or 2) carbon atoms having 1 to 10 (preferably 1 to 8, particularly preferably having 1 to 5) halogen atoms. Examples that may be mentioned are chloromethoxy, fluoro-methoxy, difluoromethoxy, trifluoromethoxy, fluoroethoxy, fluoropropoxy, and hexafluorobutoxy. Preference is given to chloromethoxy, fluoromethoxy, trifluoromethoxy, fluoroethoxy, fluoropropoxy, and hexafluorobutoxy, and particular preference is given to fluoromethoxy and trifluoromethoxy.

Halogen generally means fluorine, chlorine, bromine, or iodine, preferably fluorine, chlorine, or bromine, particularly fluorine or chlorine.

Very particularly preferred substituents for $R^1$ to $R^5$ are hydrogen, methyl, trifluoromethyl, methoxy, fluorine, or chlorine.

The process according to the invention can be used, for example, to prepare the following hydroxybenzoic benzyl esters: benzyl 2-hydroxy-benzoate (benzyl salicylate), benzyl 3-hydroxybenzoate, benzyl 4-hydroxy-benzoate, benzyl 3-chloro-2-hydroxybenzoate, benzyl 4-chloro-2-hydroxybenzoate, benzyl 5-chloro-2-hydroxybenzoate, benzyl 6-chloro-2-hydroxybenzoate, benzyl 3-bromo-2-hydroxybenzoate, benzyl 3-fluoro-2-hydroxybenzoate, benzyl 4-fluoro-2-hydroxybenzoate, benzyl 2-fluoro-3-hydroxybenzoate, benzyl 2-fluoro-4-hydroxybenzoate, benzyl 3-fluoro-2-hydroxybenzoate, benzyl 2-fluoro-5-hydroxybenzoate, benzyl 2-fluoro-6-hydroxybenzoate, benzyl 2-hydroxy-3-methylbenzoate, benzyl 2-hydroxy-4-methylbenzoate, benzyl 3-hydroxy-2-methylbenzoate, benzyl 4-hydroxy-2-methylbenzoate, benzyl 2-fluoro-6-hydroxy-4-methoxybenzoate, benzyl 3-trifluoromethyl-2-hydroxybenzoate, benzyl 4-trifluoromethyl-2-hydroxybenzoate, benzyl 2-trifluoromethyl-3-hydroxybenzoate, benzyl 2-fluoroethyl-4-hydroxybenzoate, and benzyl 4-fluorobutyl-2-hydroxybenzoate.

The benzyl chloride used in the process according to the invention is unsubstituted benzyl chloride or a substituted benzyl chloride. Particular preference is given to using unsubstituted benzyl chloride.

In the process according to the invention, it is possible to use benzyl chloride or benzyl chloride/benzyl alcohol mixtures such as are produced, for example, in the preparation of benzyl alcohol from benzyl chloride. The content of benzyl chloride in the mixture can be 50 to 100%, preferably 60 to 95%, particularly preferably 70 to 90%.

For the process according to the invention, the following hydroxy-benzoic acids may, for example, be mentioned: 2-hydroxybenzoic acid (salicylic acid), 3-hydroxybenzoic acid, 4-hydroxybenzoic acid, 3-chloro-2-hydroxybenzoic acid, 4-chloro-2-hydroxybenzoic acid, 5-chloro-2-hydroxybenzoic acid, 6-chloro-2-hydroxybenzoic acid, 3-bromo-2-hydroxybenzoic acid, 3-fluoro-2-hydroxybenzoic acid, 4-fluoro-2-hydroxybenzoic acid, 5-fluoro-2-hydroxybenzoic acid, 6-fluoro-2-hydroxybenzoic acid, 2-fluoro-3-hydroxybenzoic acid, 2-fluoro-4-hydroxybenzoic acid, 2-fluoro-5-hydroxy-benzoic acid, 2-fluoro-6-hydroxybenzoic acid, 2-hydroxy-3-methylbenzoic acid, 2-hydroxy-4-methylbenzoic acid, 3-hydroxy-2-methylbenzoic acid, 4-hydroxy-2-methylbenzoic acid, 6-hydroxy-2-fluoro-4-methoxybenzoic acid, 2-hydroxy-3-trifluoromethyl-benzoic acid, 2-hydroxy-4-trifluoromethyl-benzoic acid, 3-hydroxy-2-trifluoromethyl-benzoic acid, 4-hydroxy-2-fluoroethylbenzoic acid, 2-hydroxy-4-fluorobutyl-benzoic acid, 2-hydroxy-3-methoxybenzoic acid, 2-hydroxy-4-nitrobenzoic acid, 3-acetyl-2-hydroxybenzoic acid, or 4-cyano-2-hydroxybenzoic acid.

Preference is given to hydroxybenzoic acids having 2 to 30 carbon atoms, particularly preferably 2 to 12 carbon atoms. Very particular preference is given to salicylic acids.

The process according to the invention is preferably carried out with removal of the hydrogen chloride formed. Removal of the hydrogen chloride by passing an inert gas through, such as, for example, nitrogen, is suitable.

In the process according to the invention, preference is given to using 0.1 to 50 mol of hydroxybenzoic acid (preferably 0.5 to 30 mol, particularly preferably 1 to 20 mol), based on 1 mol of benzyl chloride.

Suitable amides are compounds of the formula

in which
$R^6$ is hydrogen, $C_1$–$C_6$-alkyl, $C_1$–$C_{10}$-aralkyl, $C_1$–$C_{12}$-aryl, $C_1$–$C_6$-alkoxy, amino, $C_1$–$C_6$-alkylamino, $C_1$–$C_6$-cycloalkylamino, or $C_1$–$C_6$-dialkyl-amino, and
$R^7$ and $R^8$ are identical or different and are hydrogen, $C_1$–$C_6$-alkyl, $C_1$–$C_6$-cycloalkyl, $C_1$–$C_{10}$-aralkyl, or $C_1$–$C_{12}$-aryl,
or $R^6$ and $R^7$ together form a group $(CH_2)_n$ or $NR^9$ $(CH_2)_n$, in which
$R^9$ is hydrogen, $C_1$–$C_6$-alkyl, $C_1$–$C_6$-cycloalkyl, $C_1$–$C_{10}$-aralkyl or $C_1$–$C_{12}$-aryl, and
n is 1 to 5.

Amides suitable for carrying out the process according to the invention are straight-chain or branched, acyclic or cyclic. Suitable compounds include amides, alkylamides, dialkylamides, cycloalkylamides, arylalkylamides, or arylamides of carboxylic acids having 1 to 30 carbon atoms, ureas or mono-, di-, tri-, or tetraalkylureas having 1 to 30 carbon atoms, and urethanes or mono- or dialkylurethanes having 1 to 30 carbon atoms.

Preference is given to formamide, N-methylformamide, N-ethyl-formamide, dimethylformamide, acetamide, methylacetamide, urea, dimethylurea, or tetramethylurea, particular preference being given to formamide, N-methylformamide, acetamide, methylacetamide, urea, dimethylurea, or tetramethylurea.

Also suitable are cyclic amides (lactams) of amino-, alkylamino-, arylamino-, hydroxyamino-, alkoxyamino-, alkoxycarbonylamino-, and alkoxycarbonylalkylaminocarboxylic acids having 1 to 30 carbon atoms.

Suitable as alkyl for such amides are straight-chain or branched, cyclic or acyclic alkyl-, aryl-, aralkyl-, hydroxyalkyl-, alkoxyalkyl- and alkoxycarbonyl radicals having 1 to 30 carbon atoms (preferably 1 to 24 carbon atoms, particularly preferably 1 to 20 carbon atoms), preferably alkyl, aralkyl, aryl, hydroxyalkyl, and alkoxyalkyl, particularly preferably alkyl, aralkyl, and hydroxyalkyl radicals.

Suitable lactams are four-, five-, six-, seven-, and higher-membered cyclic amides having 1 to 30 carbon atoms, such as, for example, 2-pyrrolidinones, 2-piperidones, and caprolactams.

Also suitable are aromatic lactams, such as, for example, 2-pyridones or 1-alkyl-2-pyridones.

The lactams used for the preparation of the catalysts according to the invention are generally obtained by cyclizing β-, γ-, δ-, or ε-amino-carboxylic acids or carboxylic esters having 1 to 30 carbon atoms, optionally in the presence of catalysts.

Suitable compounds are pyrrolidinone, N-alkylpyrrolidinone, N-cycloalkyl-2-pyrrolidinone, N-hydroxyalkyl-2-pyrrolidinone, 2-piperidone, N-alkyl-2-piperidone, N-cycloalkyl-2-piperidone, N-aryl-2-piperidone, caprolactam, N-alkyl-2-caprolactam, N-vinyl-2-caprolactam, N-hydroxy-alkyl-2-caprolactam, N-aryl-2-caprolactam, N-alkyl-2-pyridone, N-cyclo-alkyl-2-pyridone, N-hydroxyalkyl-2-pyridone, and N-aryl-2-pyridone.

Preferred lactams are 2-pyrrolidinone, N-methyl-2-pyrrolidinone, N-ethyl-2-pyrrolidinone, N-propyl-2- pyrrolidinone, N-butyl-2-pyrrolidinone, N-pentyl-2-pyrrolidinone, N-hexyl-2-pyrrolidinone, N-heptyl-2-pyrrolidinone, N-octyl-2-pyrrolidinone, N-nonyl-2-pyrrolidinone, N-decyl-2-pyrrolidinone, N-undecyl-2-pyrrolidinone, N-dodecyl-2-pyrrolidinone, N-hexadecyl-2-pyrrolidinone, N-heptadecyl-2-pyrrolidinone, N-octadecyl-2-pyrrolidinone, N-cyclopentyl-2-pyrrolidinone, N-cyclohexyl-2-pyrrolidinone, N-vinyl-2-pyrrolidinone, N-hydroxyethyl-2-pyrrolidinone, N-hydroxypropyl-2-pyrrolidinone, N-hydroxybutyl-2-pyrrolidinone, N-benzyl-2-pyrrolidinone, N-phenyl-2-pyrrolidinone, N-methyl-2-piperidone, N-ethyl-2-piperidone, N-propyl-2-piperidone, N-propyl-2-piperidone, N-cyclohexyl-2-piperidone, N-hydroxyethyl-2-piperidone, N-vinyl-2-piperidone, N-benzyl-2-piperidone, N-phenyl-2-piperidone, 2-caprolactam, N-methyl-2-caprolactam, N-ethyl-2-caprolactam, N-propyl-2-caprolactam, N-butyl-2-caprolactam, N-propyl-2-caprolactam, N-cyclohexyl-2-caprolactam, N-vinyl-2-caprolactam, N-hydroxyethyl-2-caprolactam, N-methyl-2-pyridone, N-ethyl-2-pyridone, N-propyl-2-pyridone, N-cyclohexyl-2-pyridone, N-vinyl-2-pyridone, N-benzyl-2-pyridone, N-phenyl-2-pyridone or N-hydroxyethyl-2-pyridone, particular preference being given to 2-pyrrolidinone, N-methyl-2-pyrrolidinone, N-ethyl-2-pyrrolidinone, N-cyclohexyl-2-pyrrolidinone, 2-caprolactam, N-methyl-2-caprolactam, and N-ethyl-2-caprolactam.

Methods for the preparation of amides are generally well known and, for example, are described in detail in *Römpp: Lexikon Chemie*, 10th edition, Stuttgart/New York 1997, Volume 1, page 153, Volume 2, page 1686, and Volume 3, page 2328; *Houben-Weyl: Methoden der organischen Chemie*, Volume E V/2, 4th edition, Stuttgart 1985, page 934.

The amides can be used either homogeneously or on an inert support in heterogeneous form.

The amides can be used, for example, as powders or molded bodies and can be separated off after the reaction, e.g., by distillation, filtration, sedimentation, or centrifugation.

In the case of an arrangement as a fixed bed, the amides are preferably applied to a support and used as molded bodies, e.g., as spheres, cylinders, rods, hollow cylinders, rings, and the like.

Suitable support materials are activated carbon, silica gel, aluminum oxide, aluminosilicates, such as zeolites, or phyllosilicates, clay earths, titanium oxides, and zirconium oxides.

When working with suspended catalysts, the amides are used in stirred vessels in amounts of from 0.1 to 100% by weight (preferably from 0.5 to 90% by weight and particularly preferably from 1.0 to 80% by weight), based on dibenzyl ether.

For a continuous procedure in countercurrent or cocurrent or in the trickle phase on a fluidized bed, space velocities of from 0.05 g to 5000 g of benzyl chloride per liter of immobilized amide per hour, preferably from 0.1 to 4000 g/l.h and in particularly preferably from 1.0 to 3000 g/l.h are used.

The process according to the invention is preferably carried out with intensive mixing of the reactants. Intensive mixing can be achieved in various ways known to those skilled in the art, for example by stirrers, nozzles, baffles, static mixers, pumps, or turbulent flows in narrow tubes or by ultrasound.

Such devices are described in more detail in *Ullmann's Encyclopedia of Industrial Chemistry*, 5th edition, Volume B, Unit Operations, Sections 25, 26, B4 pages 569–572, Verlag Chemie, Weinheim 1988.

The crude hydroxycarboxylic benzyl ester can be further purified, for example, by distillation or crystallization.

The process according to the invention can be carried out batchwise, continuously, or semicontinuously.

A preferred embodiment of the process according to the invention involves adding benzyl chloride to a mixture or suspension of amide, optionally applied to a support, and hydroxybenzoic acid, and, when the reaction is complete, separating off the amide or its salt by, for example, distillation, filtration, or centrifugation.

A further preferred method of implementation is the cocurrent procedure in which benzyl chloride and hydroxybenzoic acid are applied in cocurrent (for example, from the top downward) onto a supported amide bed arranged in a tube, and hydroxybenzoic benzyl ester is drawn off downstream at the foot of the tube.

A further preferred embodiment of the process according to the invention is carried out in the trickle phase and the supported amide is in the form of a fixed bed. The fixed bed is preferably located in a vertical tubular reactor which preferably contains intermediate plates to improve distribution of the liquid stream and to improve wetting of the bed.

Both in the case of the suspended catalyst and in fixed-bed process variants, work-up can be carried out by adding a solvent, preferably toluene, to the reaction products. Following filtration, the crude hydroxybenzoic benzyl ester can, for example, be further purified by distillation.

The temperature at which the process according to the invention is carried out is preferably 15 to 200° C., particularly preferably 25 to 190° C., very particularly preferably 30 to 180° C.

If the reaction is carried out above 180° C., it is necessary to work under increased pressure corresponding to the vapor pressure. The required gauge pressure is then at least equal to the vapor pressure of the reaction mixture. It may be up to about 50 bar, preferably up to 25 bar.

Where appropriate, the process according to the invention can be carried out under a customary protective gas, such as, for example, nitrogen, helium, or argon.

The process according to the invention can be illustrated by the following reaction equation:

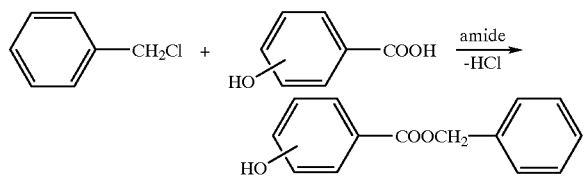

The process according to the invention gives hydroxybenzoic benzyl esters in good yields with a high conversion and good selectivity. The process according to the invention can be carried out easily without high expenditure on apparatus.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius, all percentages are percentages by weight, and all reaction mixture ratios are weight ratios.

EXAMPLES

Example 1

63.2 g (0.50 mol) of benzyl chloride were added, at 150° C. and with vigorous stirring (500 rpm), to a mixture of 69.0 g (0.50 mol) of 2-hydroxy-benzoic acid (i.e., salicylic acid) (Merck) and 45.0 g (1.0 mol) of formamide (Firma Aldrich) in a flask with baffles and paddle stirrer. After a reaction time at 150° C. of 1 h, the mixture was cooled rapidly and, following dissolution in toluene, the composition was analyzed using gas chromatography. The reaction mixture comprised benzyl chloride/benzyl salicylate in the ratio 10.5:89.5.

Example 2

Example 1 was repeated, but using 59.1 g (1.0 mol) of N-methyl-formamide (Aldrich). After a reaction time of 5 h, the reaction mixture comprised benzyl chloride/benzyl salicylate in the ratio 26.9:73.1.

Example 3

Example 1 was repeated, but using 73.0 g (1.0 mol) of dimethyl-formamide (Merck). After a reaction time of 5 h, the reaction mixture comprised benzyl chloride/benzyl salicylate in the ratio 44.2:55.8.

Example 4

Example 1 was repeated, but at 140° C. After a reaction time of 7 h, the reaction mixture comprised benzyl chloride/benzyl salicylate in the ratio 50.5:49.5.

Example 5

Example 1 was repeated, but using 59.0 g (1.0 mol) of acetamide (Acros). After a reaction time of 5 h, the reaction mixture comprised benzyl chloride/benzyl salicylate in the ratio 52.1:47.9.

Example 6

Example 1 was repeated, but using 87.0 g (1.0 mol) of dimethyl-acetamide (Aldrich). After a reaction time of 7 h, the reaction mixture comprised benzyl chloride/benzyl salicylate in the ratio 80.7:19.3.

Example 7

Example 1 was repeated, but using 73.0 g (1.0 mol) of benzamide (Acros). After a reaction time of 5 h, the reaction mixture comprised benzyl chloride/benzyl salicylate in the ratio 83.0:17.0.

Example 8

Example 1 was repeated, but using 99.1 g (1.0 mol) of 1-methyl-2-pyrrolidone (Acros). After a reaction time of 7 h, the reaction mixture comprised benzyl chloride/benzyl salicylate in the ratio 91.7:8.3.

Example 9

Example 1 was repeated, but using 113.0 g (1.0 mol) of caprolactam (Bayer). After a reaction time of 7 h, the reaction mixture comprised benzyl chloride/benzyl salicylate in the ratio 76.4:23.6.

Example 10

Example 1 was repeated, but using 127.2 g (1.0 mol) of N-methyl-caprolactam (Aldrich). After a reaction time of 7 h, the reaction mixture comprised benzyl chloride/benzyl salicylate in the ratio 87.2:12.8.

Example 11

Example 1 was repeated, but using 60.0 g (1.0 mol) of urea (Grüssing). After a reaction time of 7 h, the reaction mixture comprised benzyl chloride/benzyl salicylate in the ratio 87.2:12.8.

Example 12

Example 1 was repeated, but using 30.0 g (0.5 mol) of urea (Grüssing). After a reaction time of 3 h, the reaction mixture comprised benzyl chloride/benzyl salicylate in the ratio 7.2:92.8.

Example 13

Example 1 was repeated, but using 44.1 g (0.5 mol) of N,N-dimethylurea (Acros). After a reaction time of 1 h, the reaction mixture comprised benzyl chloride/benzyl salicylate in the ratio 40.6:59.4.

Example 14

Example 1 was repeated, but using 58.1 g (0.5 mol) of tetra-methylurea (Acros). After a reaction time of 5 h, the reaction mixture comprised benzyl chloride/benzyl salicylate in the ratio 44.1:55.9.

Example 15

Example 3 was repeated, but using 69.0 g (0.5 mol) of 3-hydroxy-benzoic acid (Acros). After a reaction time of 7 h, the reaction mixture comprised benzyl chloride/benzyl 3-hydroxyphenylcarboxylate in the ratio 55.3:44.7.

Example 15

Example 3 was repeated, but using 69.0 g (0.5 mol) of 4-hydroxy-benzoic acid (Acros). After a reaction time of 7 h, the reaction mixture comprised benzyl chloride/benzyl 4-hydroxyphenylcarboxylate in the ratio 54.5:45.5.

Example 16

Work-Up

Example 3 was repeated. After a reaction time of 7 h, the reaction mixture comprised benzyl chloride/benzyl salicylate in the ratio 31.2:68.8 and was separated off by vacuum distillation.

20.3 g of benzyl chloride (30° C./2.5 mbar) and 47.8 g of benzyl salicylate (136° C./0.5 mbar)—i.e., 61.8% benzyl salicylate, based on reacted benzyl chloride—were isolated.

Example 17

Comparative Example

Example 1 was repeated, but without amide. After a reaction time of 7 h, the reaction mixture comprised benzyl chloride/benzyl salicylate in the ratio 89.3:10.7.

What is claimed is:
1. A process for the preparation of a hydroxybenzoic benzyl ester of the formula

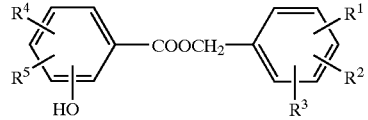

in which $R^1$ to $R^5$ are identical or different and are hydrogen, $C_1$–$C_6$-alkyl, $C_1$–$C_6$-alkoxy, $C_1$–$C_6$-halogenoalkyl, $C_1$–$C_6$-halogenoalkoxy, CN, CO($C_1$–$C_6$-alkyl), $NO_2$, or halogen, comprising reacting a benzyl chloride of the formula

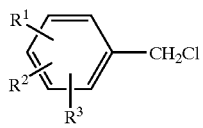

in which $R^1$, $R^2$, and $R^3$ have the meanings given above for the hydroxybenzoic benzyl ester,
or mixtures of such benzyl chlorides and a benzyl alcohol of the formula

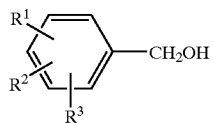

in which $R^1$, $R^2$, and $R^3$ have the meanings given above for the hydroxybenzoic benzyl ester,
with a hydroxybenzoic acid of the formula

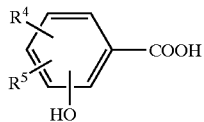

in which $R^4$ and $R^5$ have the meanings given above for the hydroxybenzoic benzyl ester,
in the presence of one or more amides of the formula

in which
$R^6$ is hydrogen, $C_1$–$C_6$-alkyl, $C_1$–$C_6$-cycloalkyl, $C_1$–$C_6$-alkoxy, amino, $C_1$–$C_6$-alkylamino, $C_1$–$C_6$-cycloalkylamino, or $C_1$–$C_6$-dialkylamino and
$R^7$ and $R^8$ are identical or different and are hydrogen, $C_1$–$C_6$-alkyl, $C_1$–$C_6$-cycloalkyl, $C_1$–$C_{10}$-aralkyl, or $C_1$–$C_{12}$-aryl,
or $R^6$ and $R^7$ together form a group $(CH_2)_n$ or $NR^9(CH_2)_n$, in which
$R^9$ is hydrogen, $C_1$–$C_6$-alkyl, $C_1$–$C_6$-cycloalkyl, $C_1$–$C_{10}$-aralkyl, or $C_1$–$C_{12}$-aryl, and
n is 2 to 6.

2. A process according to claim 1 wherein the amide is an acyclic amide.

3. A process according to claim 1 wherein the amide is a cyclic amide.

4. A process according to claim 1 wherein the amide is a urea.

5. A process according to claim 1 wherein the amide is a urethane.

6. A process according to claim 1 wherein the amide is form-amide, N-methylformamide, dimethylformamide, acetamide, N-methyl-acetamide, urea, dimethylurea, tetramethylurea, 2-pyrrolidinone, N-methyl-2-pyrrolidinone, N-ethyl-2-pyrrolidinone, N-cyclohexyl-2-pyrrolidinone, 2-caprolactam, N-methyl-2-caprolactam, or N-ethyl-2-caprolactam.

7. A process according to claim 1 wherein unsubstituted benzyl chloride is used.

8. A process according to claim 1 wherein the benzyl chloride is a substituted benzyl chloride of the formula

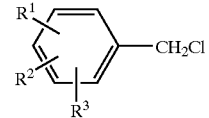

in which $R^1$ to $R^3$ are identical or different and are $C_1$–$C_6$-alkyl, $C_1$–$C_6$-alkoxy, $C_1$–$C_6$-halogenoalkyl, $C_1$–$C_6$-halogenoalkoxy, CN, $CO(C_1$–$C_6$-alkyl), $NO_2$, or halogen.

9. A process according to claim 1 wherein 0.1 to 50 mol of hydroxybenzoic acid, based on 1 mol of benzyl chloride, are used.

10. A process according to claim 1 wherein hydrogen chloride is removed by passing through nitrogen.

11. A process according to claim 1 wherein 0.1 to 10 mol of amide, based on 1 mol of benzyl chloride, are used.

12. A process according to claim 1 carried out at a temperature in the range from 10 to 200° C.

* * * * *